United States Patent [19]

Mauvais-Jarvis et al.

[11] Patent Number: 4,919,937
[45] Date of Patent: Apr. 24, 1990

[54] PERCUTANEOUS ADMINISTRATION OF TAMOXIFEN

[76] Inventors: Pierre Mauvais-Jarvis, 12, Parc de Bearn, F-92210 Saint Cloud; Frédérique Kuttenn, 6, Avenue des Gobelins, F-75008 Paris, both of France

[21] Appl. No.: 777,786

[22] PCT Filed: Dec. 21, 1984

[86] PCT No.: PCT/EP84/00436
§ 371 Date: Sep. 13, 1985
§ 102(e) Date: Sep. 13, 1985

[87] PCT Pub. No.: WO85/03228
PCT Pub. Date: Aug. 1, 1985

[30] Foreign Application Priority Data

Jan. 20, 1984 [FR] France ............................... 84 00927

[51] Int. Cl.$^5$ .................... A01N 33/02; A61K 31/135
[52] U.S. Cl. ........................................ 424/449; 514/651
[58] Field of Search ................... 424/449, 81; 514/651

[56] References Cited

FOREIGN PATENT DOCUMENTS 0002097 5/1979 European Pat. Off. .
0054168 10/1981 European Pat. Off. .
2515041 4/1983 France .

OTHER PUBLICATIONS

Chem. Abstract, vol. 85, entry 14290m, Br. J. Obstet. Gynolcol. 1976, 83(3), 183–186.
Chem. Abstracts, vol. 96, entry 62664k, Eur. J. Cancer Clin. Oncol., 1981, 17(9), 1063–1065.

*Primary Examiner*—Joseph L. Schofer
*Assistant Examiner*—Peter F. Kulkosky
*Attorney, Agent, or Firm*—Fishman, Dionne & Cantor

[57] ABSTRACT

Anti-estrogen drug of which the active product is comprised of 1 (p-dimethylaminoethoxyphenyl) trans-1-(p-hy-droxyphenyl)-2-phenylbut-1-ene, and present as a gel of the hydroalcoholic type which is percutaneously administrable. The above-mentioned active product may be associated to the progesterone. It is used for the treatment of breast affections, particularly benign cancerous affections of the breast.

2 Claims, No Drawings

PERCUTANEOUS ADMINISTRATION OF TAMOXIFEN

The present invention relates to an anti-estrogen drug which can be applied, in particular, in the treatment of certain forms of tumors, especially those of the mammary gland in their hormone-dependent forms.

At the present time, an anti-estrogen is known which can be administered orally, named tamoxifen, and consists of 1-[4-(2-N-dimethylaminoethoxy)phenyl]-1,2diphenylbut-1-(Z)-ene, which is marketed under the name "Nolvadex". However, to obtain an anti-estrogen activity at the level of the estrogen receptors, especially those of the mammary gland, it is necessary to administer per os from 10 to 30 mg per day of this compound, and this causes harmful side effects, in particular a paradoxical stimulation of the ovaries. These latter effects in large measure limit the use of tamoxifen.

It has been shown, moreover, that tamoxifen administered orally is converted during its passage through the liver to numerous metabolites, including 1-[4-(2-N-dimethylaminoethoxy)phenyl]-1-(4-hydroxy-phenyl)-2-phenylbut-1-(Z)-ene, also named 4-hydroxytamoxifen, which is the active form of the product at the molecular level. On the other hand, this 4-hydroxy derivative directly administered orally appears to be more rapidly degraded than tamoxifen and for this reason it is useless to administer it by this route. In addition, it is also known that the 4-hydroxy derivative is from twenty to one hundred times more active than tamoxifen as an anti-estrogen at the level of the estrogen receptors. However, the administration orally or parenterally, other than percutaneously, leads to a diffusion of this product throughout the organism, causing—inter alia—a detrimental paradoxical stimulation of the ovaries.

The 4-hydroxytamoxifen derivative has, indeed, been described as an anti-estrogen agent with a view to its administration orally or possibly parenterally, the administration itself being limited to injection. As mentioned above, oral administration appears to be of restricted efficacy due to the destruction of the compound itself through its passage in the liver, while injection, leading to the introduction of the said compound into the blood circulation, can induce the detrimental ovarian effects mentioned above, through a systemic effect.

The document CHEMICAL ABSTRACTS, vol. 96, No. 9, 1st Mar. 1982, page 29, abstract 62664k, COLUMBUS, OHIO (US) & Eur. J. Cancer Clin. Oncol. 1981, 17(9), 1063-5, M. SLUYSER et al., "Effect of monihydroxytamoxifen (sic) on mouse mammary tumors", describes the properties of monohydroxytamoxifen without specifying the cis or trans form, and in the context of administration as a pellet under the skin, and hence not that of percutaneous administration.

The studies of the Applicants devoted for the last 15 years to the metabolism of hormonal steriods administered percutaneously in alcoholic solution have enabled it to be demonstrated [Journal of Clinical Investigation (USA) 1970, 49 :31] that the percutaneous administration route for steroids having a short half-life permitted direct access to the target organ, whereas the oral or even intravenous administration of the same steroid favoured its metabolism in the liver at the expense of its effective concentration in the receptor tissues. The hepatic by-passes thus produced were demonstrated in the first place for testosterone [Journal of Clinical Endocrinology and Metabolism (USA) 1969, 29: 437] and then subsequently for progesterone [Journal of Clinical Endocrinology and Metabolism (USA) 1969, 29: 1590 and 1974, 38: 142 and Patent FR-A-2515041]. In the case of progesterone, it was possible to demonstrate that the administration of this steroid in alcoholic solution or in a 60% strength aqueous alcoholic gel permitted topical retention for 48 hours of the compound which had passed through the cutaneous barrier (10%). In contrast, orally, 90% of the dose administered is destroyed in the first passage through the liver.

The Applicants were hence led in their studies to try administering the 4-hydroxytamoxifen derivative percutaneously in order to avoid any systemic effect, and they were surprised to observe that, in 60% strength alcoholic solution, this compound applied on the skin overlying cancerous mammary tumors proved capable of passing through the cutaneous barrier and being taken up on the receptor molecules in these tumors. The Applicants have observed that, in contrast, tamoxifen cannot be activated to its 4-hydroxy derivative by the percutaneous route, since the breast does not have at its disposal, like the liver, the enzymes needed for the conversion.

The anti-estrogen drug according to the invention, derived from tamoxifen, the active product of which consists of 1-[4-(2-N-dimethylaminoethoxy)phenyl]-1-(4-hydroxyphenyl)-2-phenylbut-1-(Z)-ene, also named 4-hydroxytamoxifen, is presented as an aqueous alcoholic gel which can be administered percutaneously, preferably topically, and is pharmacologically acceptable.

It is accepted as common knowledge that 4-hydroxytamoxifen possesses—in addition to its property of blocking the hormonal site of the estrogen receptor (anti-estrogen action)—a stimulatory action on the receptors for another hormone involved in the good trophic quality of the breast, progesterone. In consequence, the Applicants verified that the simultaneous percutaneous administration of 4-hydroxytamoxifen and progesterone permits three complementary and synergistic actions:

an anti-estrogenic action,
stimulation of the progesterone receptor and
the occupation of the progesterone receptor by its hormone, which amplifies its activity.

In fact, progesterone binds to is own receptor, which it activates. Thus, a synergy of action is produced, since progesterone and estrogen are antagonistic at the level of their target organs.

The crossing of the cutaneous barrier by 4-hydroxytamoxifen was demonstrated using tracer doses of tritiated 4-hydroxytamoxifen applied in alcoholic solution 24 hours before the excision of cancerous breasts. Studies performed in the laboratory showed that the 4-hydroxytamoxifen appeared in its original form at the level of the protein structures corresponding to hormonal receptors. It is hence capable of having anti-estrogenic activity at this level. A small portion of the radioactivity is metabolized to unidentified products (3%). In parallel, this same product in radioactive form was applied on the skin of a healthy subject, and a calculation was made of the radioactivity appearing in the urine in 15 days following administration of the product. The rate or urinary elimination shows that there is a weak and gradual destruction of the product. In the circulating blood, only traces of the product are detectable—there is hence no accumulation. It is only as a secondary effect that it reaches the liver, where it is inactivated.

In another experiment, tracer doses of tritiated progesterone were administered under the same conditions as 4-hydroxytamoxifen. Progesterone likewise appeared in its original form, partly bound to the progesterone receptors and partly metabolized. No radioactivity circulates in the blood; in the urine, various metabolites of progesterone appeared in the 56 hours following the experiment. It may be concluded that progesterone is taken up by specific receptors and that it is inactivated for the most part in situ.

The fact that 4-hydroxytamoxifen and progesterone are soluble in alcohol and can be absorbed by the skin enables these compounds to be presented as an alcoholic gel suited to percutaneous administration, the studies of the Applicants demonstrating a coefficient of cutaneous absorption of 10% for progesterone and close to 1% for 4-hydroxytamoxifen. In a manner known per se, the alcoholic gel contains, in addition to progesterone and 4-hydroxytamoxifen, various excipients required for packaging and enabling percutaneous penetration to take place, in particular "Carbopol®", ethyl alcohol and water. The daily doses of product to be administered are easy to calculate in terms of the absorption coefficients of the drugs and the doses which it is desired to obtain for 4-hydroxytamoxifen and progesterone at the level of their receptor molecules.

A formulation for a gel according to the invention for percutaneous administration is given below, by way of an example which is in no way limitative:

| | | |
|---|---|---|
| Progesterone | 1.5 | g |
| 4-Hydroxytamoxifen | 0.15 | g |
| "Carbopol 934 ®" | 1 | g |
| Triethanolamine | 1.5 | g |
| 95% strength ethyl alcohol | 50 | ml |
| Water qs | 100 | g |

("Carbopol 934 ®" is a carboxyvinyl polymer having active carboxyl groups, contributing to form stable emulsions with amines).

These products, administered percutaneously on the breast, concentrate electively in the mammary gland and are then eliminated at negligible rates in biological fluids. The effect obtained is the reverse of that observed in the case of oral administration, where a high plasma concentration has to be obtained in order to have a low local concentration. In the case of percutaneous administration, the rates are maximal close to the site of administration, and minimal in the blood circulation and liver. This technique hence meets the stated requirement: topical anti-estrogenic medication with a possible aim of treatment (disease of the breast) and without harmful side effects.

The technique of topical 4-hydroxy-tamoxifen/progesterone administration is hence adapted in such a manner as to produce optimization of the effects of an anti-estrogen on a specific target organ. No other medication meets these standards: progesterone cannot, in fact, be used orally since it is completely destroyed during its passage through the liver.

The 4-hydroxytamoxifen/progesterone combination is capable of blocking in vitro the activity of estrogens which are factors in cell multiplication, and at the same time of improving the progesterone activity: these are synergistic and complementary actions which are not achieved with the separate administration of each of the constituents of the gel formulation mentioned above.

The preparation of 4-hydroxytamoxifen is known per se and can, for example, be carried out according to a modification of the synthesis described by Robertson and Katzenellenbogen (J. Org. Chem. 1982, 47, 2387 and J. Steroid. Biochem. 1982, 16, 1) which takes place in several stages:

(1) reaction between 4-($\beta$-dimethylaminoethoxy)-$\alpha$-ethyldeoxybenzoin and p-(2-tetrahydropyranyloxy)-phenylmagnesium bromide;

(2) separately from the above, formation of 1-(4-hydroxyphenyl)-2-phenyl-1-butanone by hydroxylation of 1,2-diphenyl-1-butanone;

(3) the reaction between the products (1) and (2) leads to the formation of: 1-(4-dimethylaminoethoxyphenyl)-1-[p-2-tetrahydro pyranyloxy)phenyl]-2-phenylbutan-1-ol;

(4) dehydration with methanol/hydrochloric acid produces 1-[p-($\beta$-dimethylaminoethoxy)phenyl]-trans-1-(p-hydroxyphenyl)-2-phenylbut-1-ene=4-OH-tamoxifen, a mixture of cis and trans isomers.

(5) separation of the cis and trans isomers by chromatography and crystallization to constant specific activity.

The drug described finds application in the treatment of conditions of the breast, especially benign and even cancerous conditions of the breast.

It is clearly understood that the present invention has only been described for the purposes of explanation and without any implied limitation, and that any useful modification can be made thereto without departing from the scope thereof.

We claim:

1. A method of treating conditions of the breast including the steps of:
    forming an aqueous alcoholic gel in which the active ingredient consists of
    1-[4-(2-N-dimethylaminoethoxy)phenyl]-1-(4-hydroxyphenyl)-2-phenylbut-1-(Z)-ene; and
    administering percutaneously said aqueous alcoholic gel as an anti-estrogen drug to a breast.

2. The method of claim 1 wherein progesterone is added to said aqueous alcoholic gel to provide a synergistic effect.

* * * * *